United States Patent [19]
Schwertner

[11] Patent Number: 5,380,667
[45] Date of Patent: Jan. 10, 1995

[54] SERUM BILIRUBIN AND LIVER FUNCTION TESTS AS RISK PREDICTORS FOR CORONARY ARTERY DISEASE

[75] Inventor: Harvey A. Schwertner, San Antonio, Tex.

[73] Assignee: The United States of America as represented by the Secretary of the Air Force, Washington, D.C.

[21] Appl. No.: 968,881

[22] Filed: Oct. 30, 1992

[51] Int. Cl.$^6$ .............................................. G01N 33/92
[52] U.S. Cl. ..................................... 436/71; 436/63; 436/86; 436/97
[58] Field of Search ............ 436/63, 97, 811, 903, 436/71, 12, 86

[56] References Cited

U.S. PATENT DOCUMENTS

| | | | |
|---|---|---|---|
| 3,715,188 | 2/1973 | Denny | 23/230 B |
| 4,464,388 | 8/1984 | Sakai et al. | 424/275 |
| 4,672,041 | 6/1987 | Jain | 436/97 |
| 4,683,208 | 7/1987 | Aoyama et al. | 436/97 |
| 4,788,153 | 11/1988 | Detwiler et al. | 436/97 |
| 4,863,873 | 9/1989 | Matson | 436/63 |
| 4,965,210 | 10/1990 | Modrovich | 436/97 |
| 5,032,608 | 7/1991 | Dudrick | 514/396 |
| 5,112,827 | 5/1992 | Saunders et al. | 514/263 |

OTHER PUBLICATIONS

Robert Berkow, The Merch Manual of Diagnosis and Therapy, 1987 p. 2413.

Y. Adachi, H. Inufusa, M. Yamashita, A. Kambe, K. Yamazaki, Y. Sawada and T. Yamamoto, Clinical Application of Serum Bilirubin Fractionation by Simplified Liquid Chromatography, 1988, vol. 34, No. 2 pp. 385–388.

B. T. Doumas and Tai–Wing Wu, The Measurement of Bilirubin Fractions in Serum, Critical Reviews in Clinical Laboratory Sciences, 1991, vol. 28 Nos. 5 and 6, pp. 415–445.

J. J. Lauff, M. E. Kasper and R. T. Ambrose, Quantitative Liquid–Chromatographic Estimation of Bilirubin Species in Pathological Serum, 1983, vol. 29, No. 5, pp. 800–805.// K. P. M. Heirwegh, J. Fevery & N. Blanckaert Chromatographic Analysis & Structure Determination of biliverdins & Bilirubins 1989, vol. 496, pp. 1–26.

Primary Examiner—James C. Housel
Assistant Examiner—N. Bhat
Attorney, Agent, or Firm—Fredric L. Sinder; Thomas L. Kundert

[57] ABSTRACT

A new series of non-lipid risk factors for predicting coronary artery disease (CAD) are disclosed. The level of serum total bilirubin was found to be a statistically significant independent risk factor for CAD and to be inversely related to CAD. Similarly, the levels of fasting blood sugar, serum glutamate pyruvate transaminase and the ratio of total cholesterol to serum total bilirubin were found to be significant univariate predictors of CAD.

3 Claims, 1 Drawing Sheet

SERUM BILIRUBIN AND LIVER FUNCTION TESTS AS RISK PREDICTORS FOR CORONARY ARTERY DISEASE

RIGHTS OF THE GOVERNMENT

The invention described herein may be manufactured and used by or for the Government of the United States for all governmental purposes without the payment of any royalty.

BACKGROUND OF THE INVENTION

The present invention relates generally to predictive tests for early onset of coronary artery disease, and more particularly to the use of serum bilirubin, fasting blood sugar and liver function tests as risk predictors for coronary artery disease.

Cholesterol, smoking, and hypertension are widely recognized as major risk factors for coronary artery disease (CAD), often referred to by the more general term coronary heart disease. Of these risk factors, cholesterol has consistently been found to have the highest association with coronary artery disease and to be its best predictor. Accordingly, much attention has been focused on cholesterol as a risk factor. More recently, a number of lipoproteins and apolipoproteins have been identified as major risk predictors and some of them, for example, high density lipoprotein (HDL) cholesterol, have been identified as independent risk factors.

A particular problem of CAD and other related heart diseases is that most individuals with heart disease are largely asymptomatic until their first heart attack. Unfortunately, the major risk factors thus far identified in the prior art are not perfect predictors, particularly for predicting the risk of coronary artery disease in any single individual. Thirty to forty percent of the population is still misdiagnosed using the known major risk factors.

Thus it is seen that there is a need for new risk factors for coronary artery disease which, in combination with prior art risk factors, will improve the predictability of coronary artery disease.

It is, therefore, a principal object of the present invention to provide coronary risk information beyond that of age, total cholesterol, HDL-cholesterol, smoking history and systolic blood pressure.

It is a feature of the present invention that it uses information generally already available from tests already routinely performed.

It is another feature of the present invention that it can be used to diagnose health or the absence of disease.

It is an advantage of the present invention that it improves specificity, sensitivity and accuracy of predictive tests for CAD.

It is another advantage of the present invention that its use will result in fewer false predictions.

It is yet another advantage of the present invention that its use will result in treatment for individuals with CAD to begin at an earlier age.

It is a further advantage of the present invention that its use of serum total bilirubin as a predictor for CAD can substitute for HDL-cholesterol, tests for which are difficult to standardize.

These and other objects, features and advantages of the present invention will become apparent as the description of certain representative embodiments proceeds.

SUMMARY OF THE INVENTION

The present invention provides new non-lipid risk factors for predicting coronary heart disease. The unique discovery of the present invention is that subacute levels of serum total bilirubin, a non-lipid, are a significant independent risk predictor for coronary artery disease. Another unique discovery is that the ratio of total cholesterol to bilirubin may be used in place of HDL-cholesterol or the ratio of total cholesterol to HDL-cholesterol as a predictor for CAD. Yet another unique discovery of the present invention is that fasting blood sugar is a significant univariate predictor of CAD and that subacute levels of several liver function enzymes are almost as significant predictors of CAD.

Accordingly, the present invention is directed to a method for determining the likelihood that a patient now has or will develop in the future severe coronary artery disease, comprising the steps of measuring the level of the patient's serum total bilirubin, comparing the measured level to a threshold level for serum total bilirubin, and determining from the comparison the likelihood that the patient now has or will develop severe coronary artery disease. The threshold level of serum total bilirubin may be 0.6 mg/dl, wherein levels below 0.6 mg/dl indicate that the patient likely now has or will develop severe coronary artery disease.

The present invention is also directed to an improvement to the method for determining the likelihood that a patient now has or will develop severe coronary artery disease, comprising the steps of measuring and comparing to threshold levels the age, total cholesterol, HDL-cholesterol, smoking history and systolic blood pressure of the patient, wherein the improvement comprises measuring the level of the patient's serum total bilirubin and comparing the measured level to a threshold level for serum total bilirubin. The threshold level of serum total bilirubin may be 0.6 mg/dl, wherein levels below 0.6 indicate that the patient likely now has or will develop severe coronary artery disease.

The present invention is further directed to a compartmentalized kit for detecting persons at an increased risk for coronary artery disease, comprising a first container adapted to contain a reagent for measuring serum total bilirubin and a first label indicating the suitability of the kit for predicting whether a patient likely now has or will develop coronary artery disease.

The present invention is yet further directed to a method for determining the likelihood that a patient now has or will develop in the future severe coronary artery disease, comprising the steps of measuring the level of the patient's fasting blood sugar or serum glutamate pyruvate transaminase, or the ratio of the patient's total cholesterol to serum bilirubin, comparing the measured level or ratio to a threshold level or ratio for fasting blood sugar, serum glutamate pyruvate transaminase or the ratio of total cholesterol to serum bilirubin, and determining from the comparison the likelihood that the patient now has or will develop severe coronary artery disease.

The present invention is still further directed to a compartmentalized kit for detecting persons at an increased risk for coronary artery disease, comprising a first container adapted to contain a reagent for measuring fasting blood sugar, serum glutamate pyruvate transaminase or serum glutamate oxalacetate transaminase and a first label indicating the suitability of the kit for predicting whether a patient likely now has or will develop coronary artery disease. The compartmentalized kit may also comprise a first container adapted to contain a reagent for measuring total cholesterol, a second container adapted to contain a reagent for measuring serum total bilirubin and a first label indicating the suitability of the kit for predicting whether a patient likely now has or will develop coronary artery disease.

DESCRIPTION OF THE DRAWING

The present invention will be more clearly understood from a reading of the following detailed description in conjunction with the accompanying drawing wherein.

DETAILED DESCRIPTION

Figure 1:
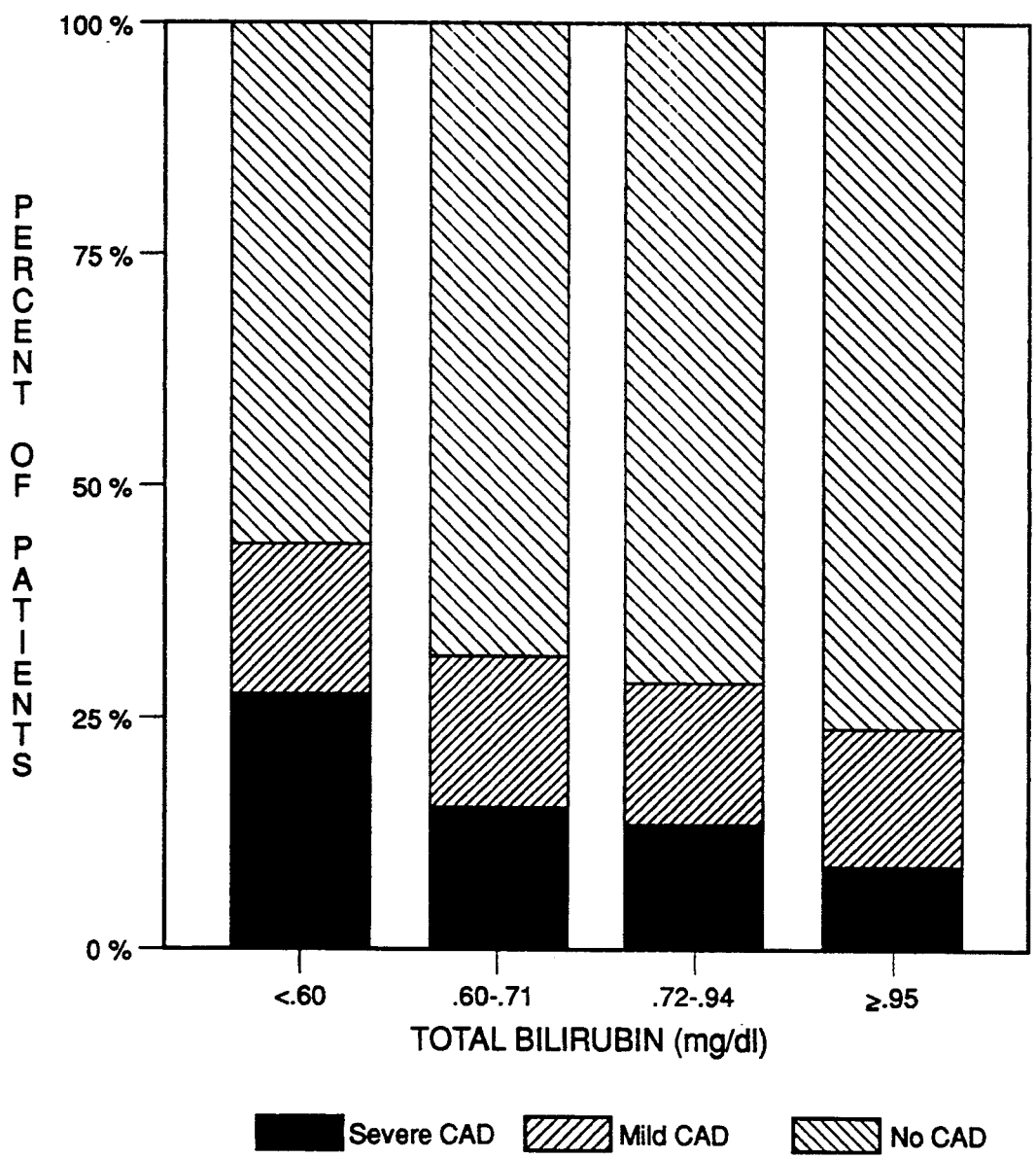
FIG. 1 is a bar graph of a univariate representation of the relationship between the prevalence of coronary artery disease and total serum bilirubin.

A study was conducted to investigate a number of clinical laboratory tests, other than those for lipids and lipoproteins, to see if they might be related to the presence or absence of coronary artery disease. A particular interest of the study was liver function tests because the liver is the key site for the synthesis and metabolism of lipids and lipoproteins, and because secondary liver disease is often associated with increases in lipids and lipoproteins. Also, because cholesterol and LDL-cholesterol are cleared by the liver, individuals with subacute forms of liver disease might have a decreased clearance of cholesterol and more CAD.

FIG. 1 summarizes some of the results of the study. It shows a bar graph of a univariate representation of the relationship between the prevalence of coronary artery disease and the level of serum total bilirubin in a study of 877 patients. Coronary artery disease is defined by maximum percent arterial obstruction: Severe (>50%), mild (10–49%), and none (<10%). For 229 patients with total bilirubin <0.60 mg/dl, 63 (27.5%) had severe, 38 (16.6%) had mild, and 128 (55.9%) had no CAD. For 196 patients with total bilirubin from 0.60 to 0.71 mg/dl, the numbers and percentages were 30 (15.3%), 30 (15.3%) and 136 (69.4%). For 232 patients from 0.72 to 0.94 mg/dl, the numbers and percentages were 31 (13.4%), 36 (15.5%), and 165 (71.1%). For 220 patients whose total bilirubin was 0.95 or higher, the numbers and percentages were 22 (10.0%), 30 (13.6%), and 168 (76.4%).

A series of serum liver function enzymes (SGOT, SGPT, ALKP and LDH) and serum total bilirubin were examined for the study as indices of liver function, as well as the traditional coronary risk factors of age, total cholesterol, high-density lipoprotein cholesterol (HDL-cholesterol), smoking history, systolic blood pressure, triglycerides, and fasting blood sugar. Specifically sought was a determination if any of the liver function tests and coronary risk information beyond that of age, total cholesterol, HDL-cholesterol, smoking history, and systolic blood pressure.

Serum total bilirubin was found to be a statistically significant independent risk factor for CAD and to be inversely related to CAD. Its association with CAD was found to be similar to that of HDL-cholesterol, smoking, and systolic blood pressure. Bilirubin, however, was not as strong a risk factor as age or cholesterol. The prior art has not previously recognized an association between low bilirubin concentrations and a specific disease. Generally, low serum bilirubin concentrations have been associated with health and only high concentrations have had any diagnostic significance.

Serum bilirubin is derived primarily from the degradation of hemoglobin, although some originates from the erythroid elements in the reticuloendothelial cells of bone marrow, spleen, and liver.

STUDY METHODS

United States Air Force (USAF) pilots and navigators over age 35 are routinely given a resting 12-lead electrocardiogram test during their biennial physical examination. These tracings are over-read by an internist at the USAF Central EGG Library located at Brooks Air Force Base, Texas. Abnormalities are compared to a baseline tracing obtained before age 28. Aviators with serial changes, such as non-specific ST-T wave changes, undergo symptom limited treadmill exercise tolerance tests. Those with repolarization or rhythm abnormalities on stress testing are referred to the USAF Aeromedical Consultation Service also at Brooks Air Force Base. Aviators over age 30 referred for various ophthalmologic, otolaryngologic, psychiatric, or neurologic evaluations also undergo cardiovascular screening tests. These aviators are asymptomatic or very rarely have atypical angina.

Exercise Test Procedures

Each patient in the study group underwent a complete cardiovascular screen as well as an evaluation of their reason for referral. The cardiovascular screen included an electrocardiogram at rest, at least 16 hours of ambulatory electrocardiographic monitoring, a symptom limited treadmill test, cardiac fluoroscopy (beginning Oct. 1, 1982) and a thorough history and physical examination including routine blood tests.

The symptom limited treadmill exercise tests were performed after an overnight fast. The treadmill tests were interpreted as abnormal if a horizontal or downsloping ST segment depression of 1.0 mm or more occurred for at least 80 msec from the J point. Patients determined to be at risk for coronary artery disease had a repeat symptom limited treadmill test with injection of thallium 201 one minute before peak exercise, followed immediately by scanning for 30 minutes and four hours post-exercise. Cardiac catheterization and coronary arteriography were performed for abnormal repolarization, decreased thallium uptake, cardiac calcification on fluoroscopy, tachycardia (three or more consecutive ectopic beats), acquired left bundle branch block or valvular abnormalities.

Coronary Angiography

In most cases, coronary arteriography was performed using the Judkins technique. Each arteriogram was read jointly by at least two cardiologists. Coronary artery lesions were magnified, traced and carefully measured with calipers to determine the percentage diameter narrowing of the artery. A total of 877 USAF aircrew members undergoing coronary angiography between Aug. 1, 1978 and May 8, 1990 were included in this study.

Laboratory Tests

Total cholesterol and HDL-cholesterol were measured after a 14-hour overnight fast on the first day of the evaluation. High-density lipoproteins were determined by enzymatic methods after precipitation of low and very low-density lipoproteins with dextran-sulfate or phosphotungstate-magnesium reagents. The cholesterol assays were calibrated against the Abell-Kendall method using cholesterol standards obtained from the National Institute of Standards and Technology in Gaithersburg, Md. Triglycerides were analyzed enzymatically without corrections for endogenous glycerol concentrations. All of the other tests, for example, liver enzymes, bilirubin, etc., were calibrated against standards supplied by the reagent manufacturer.

Between day coefficients of variation (CVs) for cholesterol (200 mg/dl) and HDL-cholesterol (50 mg/dl) were approximately 2% and 5%, respectively. Between day CVs for bilirubin, triglycerides and the serum liver enzymes were in the range of 5–10%, depending on their concentration or activity level. The laboratory performing the tests participated in both intra- and inter-laboratory quality control programs sponsored by the College of American Pathologists. Quality control met the highest standards of the College of American Pathologists.

Patient Groups

For 258 of the 877 subjects in this study, information on one or another of the risk factors to be considered was not available. Since variable selection procedures require complete data, the patients were divided into a training group of 619 for whom data were complete and the other 258 were saved to test the most complete sub-model possible, based on the risk factors selected in the analysis of the 619.

Statistical Methods

Polytomous logistic regression models were fitted using SAS PROC LOGISTIC, available from SAS Institute, Inc., Cary, N.C. Coronary disease was divided into three levels according to the maximum coronary obstruction at angiography: <10% (no gradeable disease), at least 10% but less than 50% (mild disease), and 50% or greater (severe disease). All of the independent variables, including systolic blood pressure and fasting serum glucose, were treated as continuous variables. Cigarette smoking was measured in pack-years, the reported average number of packs of cigarettes smoked per day multiplied by the number of years smoked. Independent variables with coefficient of skewness greater than 2.0 (total bilirubin, triglycerides, SGPT and SGOT) were transformed logarithmically in all the regressions. In the analysis of the 619 patients with complete data, variables were entered stepwise based on the likelihood ratio test described in Hosmer and Lemeshow, Applied Logistic Regression, John Wiley and Sons, Inc., 1989, pp. 13–18 and 106–114. From the variables selected, a sub-model including those variables for which the remaining 258 patients had complete data was tested.

Variable selection was also examined on the training set of 619 by linear regression, with maximum percent obstruction as a continuous variable using SAS PROC RSQUARE. In addition, the Mantel-Haenszel odds ratio for association between CAD (severe vs. mild or none) and total bilirubin (<0.60 vs. >0.60), adjusted for other categorized covariates, was estimated using SAS PROC FREQ.

RESULTS

Patient Groups and Angiographic Data

Summary statistics for the two groups are given in Table I. In the training group of 619 patients, 111 (18%) had severe CAD, 87 (14%) had mild CAD, and 421 (68%) were free of CAD. In the test group of 258 subjects, 35 (14%) had severe CAD, 47 (18%) had mild CAD, and 176 (68%) had no CAD. Table II shows summary statistics by level of CAD for the training group.

TABLE I

| | Summary Statistics for Study Subjects | | | | | | | |
|---|---|---|---|---|---|---|---|---|
| | Subjects Without Missing Values, N = 619 (*) | | | | Subjets With Missing Values (*) | | | |
| Variable | Mean | Min | Max | Coef of Skewness | N | Mean | Min | Max |
| Age | 41.77 | 21 | 61 | −.10 | 258 | 43.71 | 23 | 65 |
| Chol | 214.5 | 117 | 473 | .87 | 258 | 217.0 | 113 | 367 |
| HDL-C | 45.75 | 20 | 96 | .84 | 258 | 41.77 | 14 | 79 |
| Pack-Yr | 10.96 | 0 | 90 | 1.52 | 96 | 11.64 | 0 | 60 |
| Sys BP | 126.9 | 94 | 182 | .55 | 52 | 125.6 | 98 | 160 |
| Tot Bili | .8259 | .20 | 3.26 | 2.17 | 258 | .7923 | .29 | 2.30 |
| Trig | 144.0 | 18 | 972 | 2.82 | 258 | 160.3 | 39 | 1848 |
| Chol/HDL-C | 4.986 | 2.1 | 14.9 | 1.35 | 258 | 5.589 | 2.3 | 11.8 |
| Fast Bl Sug | 101.6 | 72 | 153 | .72 | 258 | 100.8 | 77 | 141 |
| SGFT | 26.50 | 4 | 159 | 2.93 | 254 | 25.94 | 7 | 128 |
| SGOT | 22.34 | 6 | 94 | 2.60 | 255 | 23.44 | 6 | 64 |
| ALKP | 50.42 | 15 | 111 | 1.03 | 254 | 59.28 | 26 | 137 |
| LDH | 155.7 | 65 | 251 | .19 | 250 | 145.5 | 83 | 247 |

(*) Maximum percent obstructions for 619 subjects with complete data were: <10% (N = 421, 68%); 10%–49% (N = 87, 14%); and 50%–100% (N = 111, 18%). For 258 subjects having incomplete data these were: <10% (N = 176, 68%); 10%–49% (N = 47, 1 8%); and 50%–100% (N = 35, 14%).

| Variable | Units | |
|---|---|---|
| Age | Years | |
| Chol | raw/dl | Full name - total cholesterol |
| HDL-C | mg/dl | Full name - HDL cholesterol |
| Pack-Y | (average packs of cigs per day) * | (years smoked) = packs*years |
| Sys BP | | Supine systolic blood pressure: treadmill test |
| Tot Bil | mg/dl | Total bilirubin |
| Trig | mg/dl | Triglycerides |
| Chol/HDL-C | unitless quantity | (Total cholesterol)/(HDL cholesterol) |
| Fast Bl Sug | mg/dl | Fasting blood sugar |
| SGPT | units/liter | Full name = Serum |

TABLE I-continued

| | Summary Statistics for Study Subjects | | | | | | | |
|---|---|---|---|---|---|---|---|---|
| | Subjects Without Missing Values, N = 619 (*) | | | | Subjets With Missing Values (*) | | | |
| Variable | Mean | Min | Max | Coef of Skewness | N | Mean | Min | Max |
| SGOT | units/liter | | | glutamate pyruvate transminase Full name = Serum glutamate oxalacetate transaminase | | | | |
| ALKP | units/liter | | | Full name = alkaline phosphatase | | | | |
| LDH | units/liter | | | Full name - lactic dehydrogenase | | | | |

TABTE II

| | Summary Statistics for Subjects with No CAD, Minimal CAD, and Significant CAD (N-619) | | |
|---|---|---|---|
| Variable | No CAD (N = 421) X ± SD | Minimal CAD (N = 87) X ± SD | Significant CAD (N = 111) X ± SD |
| Age | 39.98 ± 6.22 | 45.70 ± 5.41 | 45.46 ± 5.47 |
| Chol | 205.96 ± 38.57 | 227.43 ± 32.25 | 236.81 ± 43.90 |
| HDL-C | 46.71 ± 12.04 | 44.79 ± 9.84 | 42.8 ± 69.52 |
| Pack-Yr | 8.33 ± 12.64 | 15.73 ± 16.28 | 17.19 ± 16.67 |
| Sys BP | 125.69 ± 13.23 | 127.21 ± 13.55 | 131.09 ± 13.54 |
| Tot Bill | 0.86 ± 0.42 | 0.77 ± 0.29 | 0.73 ± 0.34 |
| Trig | 138.02 ± 98.32 | 149.17 ± 78.87 | 162.58 ± 74.74 |
| Chol/HDL-C | 4.72 ± 1.63 | 5.30 ± 1.28 | 5.76 ± 1.59 |
| Past Bl Sug | 100.92 ± 10.14 | 101.64 ± 8.97 | 104.35 ± 11.08 |
| SGPT | 25.82 ± 16.23 | 26.24 ± 13.33 | 29.27 ± 19.30 |
| SGOT | 22.00 ± 9.34 | 21.54 ± 7.35 | 24.26 ± 13.83 |
| Alk Phos | 50.15 ± 14.86 | 51.76 ± 14.04 | 50.41 ± 11.70 |
| LDH | 155.81 ± 26.93 | 154.66 ± 27.18 | 156.06 ± 27.51 |

Logistic Regression Models

The results of the univariate and multivariate polytomous logistic regression modeling on the training set of 619 subjects are shown in Table III. All of the univariate variables were significant at or near the 0.05 level except for ln(SGOT), alkaline phosphatase, and lactate dehydrogenase. Stepwise logistic regression selected a model that included age, total cholesterol, HDL-cholesterol, smoking pack-years, systolic blood pressure, and ln(total bilirubin).

pendent variables for which complete data were available are included. In the multivariate model the four variables, age, total cholesterol, HDL-cholesterol, and ln(total bilirubin) were forced into the model, while in(trig), cholesterol/(HDL-chol), and fasting glucose were tested for inclusion. Once again, in(total bilirubin) was found to be significantly (and negatively) associated with prevalence of CAD.

TABLE III

| | Polytomous Logistic Regression Models: Risk (*) of Minimal and Major Coronary Artery Disease in 619 Subjects with No Missing Values (Maximum Obstruction >=10% and >=5%) (a) | | | | | |
|---|---|---|---|---|---|---|
| | Univariate | | Multivariate | | | |
| Variable | Likelihood ratio chi-sq(1 df) | P value | Likelihood ratio chi-sq(1 df) | P value | Parameter estimate | Variable Std err |
| Intercept 1 | | | | | −8.1282 | 1.6092 |
| Intercept 2 | | | | | −9.1019 | 1.6192 |
| Age | 101.61 | <.001 | 58.12 | <.001 | .122451 | .017173 |
| Chol | 62.93 | <.001 | 37.32 | <.001 | .014672 | .002451 |
| HDL-C | 10.96 | <.001 | 5.18 | .0229 | −.019723 | .008797 |
| Pack-Yr | 40.59 | <.001 | 6.10 | .0135 | .015377 | .006269 |
| Sys BP | 12.23 | <.001 | 5.74 | .0166 | .016751 | .007105 |
| ln(100*Tat Bil) | 16.31 | <.001 | 5.91 | .0151 | −.592045 | .243390 |
| ln(Trig) | 17.62 | <.001 | 1.53 | .2166 | | |
| Chol/HDL-C | 40.06 | <.001 | 2.70 | .1000 | | |
| Past Bl Sug | 8.30 | .0040 | .053 | .8179 | | |
| ln(SGPT) | 3.93 | .0655 | 1.38 | .2401 | | |
| ln(SGOT) | 1.41 | .2342 | .77 | .3790 | | |
| ALKP | .30 | .5812 | .015 | .9025 | | |
| LDH | .007 | .9315 | 1.46 | .2263 | | |

(*)Risk = 1/[1 + exp(-Intercept-B1*Age-B2*Chol - ... - B6*ln(100*Tot Bil))] where Intercept 1 gives risk that obstruction >=10% and Intercept 2 gives risk that obstruction >=50%.
(a)Multivariate modal selected by SAS PROC LOGISTIC, with variables entered stepwise. Above the line are likelihood ratio chi-squares for deletion on with 1 degree of freedom; below are chi-squares for inclusion at the final step with 1 degree of freedom. Maximum likelihood estimates with standard errors are shown for retained variables.

Table IV shows test results from fitting one submodel to the test set of 258 subjects. The subset of inde-

TABLE IV

Likelihood Ratio Test Results from Polytomous Logistic Regression Models for Selected Risk Factors Using 258 Subjects Omitted from the Main Analysis Due to Missing Data (a)

| | Univariate | | Multivariate | |
|---|---|---|---|---|
| Variable | Likelihood ratio chi-sq (1 df) | P value | Likelihood ratio chi-sq (1 df) | P value |
| Age | 20.47 | <.001 | 11.45 | <.001 |
| Chol | 30.78 | <.001 | 25.78 | <.001 |
| HDL-C | 24.77 | <.001 | 20.65 | <.001 |
| ln(Tot Bil) | 9.52 | .0020 | 12.31 | <.001 |
| ln(Trig) | -30.75 | <.001 | 1.783 | .1818 |
| Chol/HDL-C | 41.92 | <.001 | 0.487 | .4853 |
| Fast Bl Sag | 2.10 | .1472 | 0.217 | .6413 |

(a) Above the line are likelihood ratio chi-squares for deletion with 1 degree of freedom; below are chi-squares for inclusion at the final step with 1 degree of freedom.

To check whether the observed association might be due to some fluke in the data (such as a few extreme values), polytomous logistic regressions were performed on mutually exclusive subsets of subjects, balanced with respect to CAD prevalence and with respect to levels of the covariates. The standardized regression parameter estimates from these analyses are shown in Table V. There was good consistency across the subsets, indicating that the inverse association between CAD and total bilirubin was pervasive in the data set. Not only do the sign and magnitude of the regression coefficients for total bilirubin show good consistency, but since these are standardized regression coefficients, the strength of the association relative to the other risk variables can be assessed. In the data set, the association between CAD and total bilirubin was about the same level as between CAD and either HDL-cholesterol, smoking as measured by pack-years, or systolic blood pressure.

TABLE V

Standardized Logistic Regression Coefficients From Mutually Exclusive Subsets (*)

From the 619 subjects with "complete" data (N = 88 or 89)

| | AGE | CHOL | HDL | PACK-YR | SYS-BP | LN-TOTBL |
|---|---|---|---|---|---|---|
| | 0.534 | 0.392 | -0.400 | 0.316 | 0.265 | -0.225 |
| | 1.088 | 0.242 | 0.304 | 0.435 | 0.273 | -0.318 |
| | 0.605 | 0.484 | -0.450 | 0.497 | 0.224 | -0.186 |
| | 0.986 | 0.777 | -0.394 | 0.257 | 0.266 | -0.116 |
| | 0.978 | 0.817 | -0.100 | 0.096 | 0.114 | -0.132 |
| | 0.853 | 0.658 | -0.393 | -0.002 | 0.224 | -0.224 |
| | 0.772 | 0.904 | -0.189 | -0.023 | 0.498 | -0.550 |
| Mean | 0.831 | 0.610 | -0.232 | 0.225 | 0.266 | -0.250 |
| Std. Dev | .206 | .244 | .269 | .207 | .116 | .148 |
| t (6 DF) | 10.67 | 6.61 | -2.28 | -2.88 | 6.08 | -4.47 |
| P-value | <.001 | <.001 | .063 | .028 | <.001 | .004 |

From all 877 subjects: Seven subsets (N = 88 or 89) from the 619 subjects with "complete" data, plus three subsets (N = 86) from the 258 subjects with "incomplete" data.

| | AGE | CHOL | HDL | LN-TOTBL |
|---|---|---|---|---|
| | 0.661 | 0.428 | -0.350 | -0.233 |
| | 1.100 | 0.369 | 0.250 | -0.401 |
| | 0.829 | 0.491 | -0.528 | -0.240 |
| | 1.038 | 0.836 | -0.334 | -0.210 |
| | 1.025 | 0.849 | -0.126 | -0.153 |
| | 0.862 | 0.683 | -0.398 | -0.248 |
| | 0.795 | 0.829 | -0.169 | -0.449 |
| | 0.555 | 0.832 | -0.775 | -0.594 |
| | 0.263 | 1.207 | -0.717 | -0.654 |
| | 0.582 | 0.372 | -0.826 | -0.426 |
| Mean | 0.771 | 0.689 | -0.397 | -0.361 |
| Std. Dev | .260 | .272 | .333 | 0.171 |
| t (9 DF) | 9.38 | 8.02 | -3.78 | -6.67 |
| P-Value | <.001 | <.001 | .004 | <.001 |

(*) Subsets of the 619 subjects with "complete" data, balanced on CAD prevalence and level of risk factors, were formed by sorting on CAD level (None, Mild, Severe) as the "outside" sort and on the first principal of the six risk factors as the "inside, sort, and then assigning every seventh subject to the 9- subset. The 258 subjects with "incomplete, data were similarly divided into three subsets. Risk factors were then standardized to a mean of 0 and standard subset prior to regression.

Both the training set of 619 and the test set of 258 were also subdivided into subsets based on those whose liver function tests all fell into their normal ranges and those who had at least one abnormal test. The normal ranges were: 0.2–1.2 mg/dl for total bilirubin, 1–175 units/liter for lactate dehydrogenase, 1–42 units/liter for SGPT, 1–35 unit/liter for SGOT, and 1–90 units/liter for alkaline phosphatase. The adjusted P-values for ln(total bilirubin) in the four subsets from multivariate tests on models such as those in Tables III and IV were somewhat inconsistent, as follows: Normal subset of 619 (P-value=0.992), abnormal subset of 619 (P-value=0.0011), normal subset of 258 (P-value=0.0062), and abnormal subsets of 258 (P-value=0.0387).

Other Modeling Approaches

The training set of 619 subjects was reanalyzed using linear regression. The data was the same as for logistic regression except that maximum percent coronary obstruction was in its original continuous form as recorded on angiography. SAS PROC RSQUARE was used to pick the model that minimized Mallows CP statistic. The only result that differed from stepwise logistic regression was that, after the inclusion of ln(total bilirubin), ln(triglycerides) was included in the last step. The increase in R-square with the inclusion of ln(total bilirubin) was from 0.199 to 0.205, indicating that for purposes of predicting maximum percent obstruction in individuals, the total unexplained variability in linear regression models is not much reduced.

In the discrete analysis of the 619 subjects that was carried out, CAD was divided only into two levels, severe CAD or mild/no CAD; ln(total bilirubin) was bifurcated into values <0.6 and >=0.6; age was split into <35, 35–44, and >=45; total cholesterol was divided into <200, 200–220, and >220; HDL-cholesterol was taken as <45 or >=45; cigarette smoking was broken up into current smokers, those who had quit, and never smoked; and systolic blood pressure was <=140 vs. >140. Having arranged the tables so that an odds ratio greater than 1.0 indicated an inverse association between CAD and total bilirubin, we used SAS PROC FREQ to compute a Mantel-Haenszel odds ratio of 2.02 averaged over all combinations of the other variables. The Mantel-Haenszel test for an odds ratio different from 1 yielded a chi-square of 8.14 (1 df), P-value=0.004. The test-based 95% confidence limits were 1.25 to 3.27.

Analysis of the data also reveals that the ratio of total cholesterol to serum total bilirubin may also be used as a predictor for CAD, particularly in place of using HDL-cholesterol or the ratio of total cholesterol to HDL-cholesterol. The advantage of using serum total bilirubin in place of HDL-cholesterol is that it is difficult to standardize tests for HDL-cholesterol.

As previously stated, serum bilirubin is derived primarily from the degradation of hemoglobin, although some originates from the erythroid elements in the reticuloendothelial cells of bone marrow, spleen, and liver. In serum, bilirubin occurs in both the unconjugated free form as well as in the conjugated form. Each of these fractions will need to be analyzed in the future to determine which is most predictive of CAD. Ongoing improvements in testing for bilirubin precursors and metabolites (such as biliverdin) and for various bilirubin fractions and subfractions (both conjugated and unconjugated forms, and both bound and unbound) may improve the predictive value of these tests. Those with skill in the art of the invention will recognize that serum bilirubin precursors, metabolites and subfractions may be as predictive or more predictive as serum total bilirubin. Those with skill in the art of the invention will also recognize that, for best results in practicing the invention, the methods used to determine serum bilirubin will need to be standardized across labs and the precision with which bilirubin is analyzed will need to be improved. The described study was based on laboratory results obtained over an 11 year period. During that period, considerable improvements were made in the precision with which cholesterol and HDL-cholesterol were analyzed. If the precision with which bilirubin is analyzed can be improved so that it approaches the precision with which cholesterol is analyzed, the association of bilirubin and CAD can be considerably improved.

This study did not include women or older men since they were not available. Those with skill in the art, however, will see that similar results are likely to be found with these other groups. Similarly, bilirubin will likely also be valuable as a predictor of future coronary heart disease, and not just present coronary heart disease. The selection process used in this study was also different from those used in other angiographic studies. For example, the prevalence of disease in the study group was less than 18 percent, whereas the prevalence of disease in other angiographic studies was usually greater than 70 percent.

This study did not show if bilirubin has a role in preventing CAD. If the association found in this case series is confirmed by other investigations in independent study groups, then studies to elucidate a pathogenic mechanism are needed. Bilirubin is, however, an effective antioxidant, possibly protecting lipids and lipoproteins against oxidation and against plaque formation in humans. Those with skill in the art will see, therefore, that increasing bilirubin may aid in preventing CAD. Similarly, the levels of other antioxidants, such as Vitamins A, C and E, may prove useful as predictors for CAD.

The disclosed new method for predicting the presence now or in the future of CAD successfully demonstrates the use of serum bilirubin, fasting blood sugar, and other liver function tests as risk predictors for coronary artery disease. Although the disclosed methods are specialized, their teachings will find application in other areas where careful analysis of existing factors may reveal their suitability as predictive factors for medical diseases, mechanical devices and industrial processes.

It is understood that various modifications to the invention as described may be made, as might occur to one with skill in the field of the invention, within the scope of the claims. Therefore, all embodiments contemplated have not been shown in complete detail. Other embodiments may be developed without departing from the spirit of the invention or from the scope of the claims.

I claim:

1. A method for determining the likelihood that a patient is at increased risk for severe coronary artery disease, comprising the steps of:
   (a) measuring the level of the patient's serum total bilirubin;
   (b) comparing the measured level to a threshold level for serum total bilirubin; and,
   (c) determining from the comparison the likelihood that the patient is at increased risk for severe coronary artery disease wherein levels below the threshold level of serum total bilirubin indicate that the patient is at increased risk for severe coronary artery disease.

2. The method for determining that a patient is at increased risk for severe coronary artery disease according to claim 1, wherein the threshold level of serum total bilirubin is 0.6 mg/dl, and wherein levels below 0.6 mg/dl indicate that the patient is at increased risk for severe coronary artery disease.

3. A method for determining the likelihood that a patient is at increased risk for severe coronary artery disease, comprising the steps of:
   (a) measuring the ratio of the level of the patient's total cholesterol to the level of the patient's serum total bilirubin;
   (b) comparing the measured level to a threshold ratio of total cholesterol to serum total bilirubin; and,
   (c) determining from the comparison the likelihood that the patient is at increased risk for severe coronary artery disease wherein ratios above the threshold of total cholesterol to serum total bilirubin indicate that the patient is at increase risk for severe coronary artery disease.

* * * * *